United States Patent
Hasegawa

(10) Patent No.: US 7,963,167 B2
(45) Date of Patent: Jun. 21, 2011

(54) ULTRASONIC PROBE

(75) Inventor: Yasunobu Hasegawa, Saitama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 419 days.

(21) Appl. No.: 12/223,352

(22) PCT Filed: Feb. 16, 2007

(86) PCT No.: PCT/JP2007/053328
§ 371 (c)(1), (2), (4) Date: Jul. 29, 2008

(87) PCT Pub. No.: WO2007/125672
PCT Pub. Date: Nov. 8, 2007

(65) Prior Publication Data
US 2009/0049914 A1    Feb. 26, 2009

(30) Foreign Application Priority Data
Mar. 30, 2006  (JP) ................................ 2006-094853

(51) Int. Cl.
*G01N 29/24* (2006.01)
(52) U.S. Cl. .......... 73/632; 600/443; 600/444; 600/445
(58) Field of Classification Search ............... 73/632, 73/633, 644; 600/443, 444, 445, 446, 447
See application file for complete search history.

(56) References Cited

U.S. PATENT DOCUMENTS

| 4,316,271 A | * | 2/1982 | Evert | 367/140 |
| 4,466,443 A | * | 8/1984 | Utsugi | 600/463 |
| 4,785,819 A | * | 11/1988 | Pearce | 600/446 |
| 4,807,634 A |   | 2/1989 | Enjoji et al. | |
| 5,088,495 A | * | 2/1992 | Miyagawa | 600/446 |
| 5,531,119 A | * | 7/1996 | Meyers | 73/661 |

FOREIGN PATENT DOCUMENTS

EP  0 089 131 A  9/1983

(Continued)

OTHER PUBLICATIONS

European Search Report issued Mar. 23, 2009.

(Continued)

*Primary Examiner* — Hezron Williams
*Assistant Examiner* — Rose M Miller
(74) *Attorney, Agent, or Firm* — Scott D. Wofsy; Edwards Angell Palmer & Dodge LLP

(57) ABSTRACT

An ultrasonic probe is configured such that: a piezoelectric element group is housed within a sealed container so as to be rotated and oscillated left and right about a center line that equally divides a plate surface of the piezoelectric element group; and the sealed container is filled with a liquid that serves as an acoustic medium, and in the sealed container there are provided an inlet hole for the liquid as well as an exhaust hole, to the inlet hole there is connected a flexible tube that functions as a diaphragm, and on the flexible tube and the exhaust hole there are respectively provided sealing lids. As a result, there is provided an ultrasonic probe that prevents an occurrence of air bubbles in a liquid that serves as an ultrasonic wave medium, and that realizes excellent ultrasonic characteristics.

6 Claims, 5 Drawing Sheets

FOREIGN PATENT DOCUMENTS

| | | | |
|---|---|---|---|
| JP | 62-179439 A | | 8/1987 |
| JP | HEI03-184532 | | 8/1991 |
| JP | HEI7-38851 | | 5/1995 |
| JP | 2001 327500 A | | 11/2001 |
| JP | 2001327500 A | * | 11/2001 |
| JP | 2003-175033 | | 6/2003 |
| JP | 2004 141428 A | | 5/2004 |
| JP | 2005-334107 | | 12/2005 |
| JP | 2006-346125 | | 12/2006 |
| WO | WO 2004/082482 A1 | | 9/2004 |
| WO | WO 2005/094690 | | 10/2005 |

OTHER PUBLICATIONS

International Search Report of PCT/JP2007/053328 mailed by the ISA on Jul. 17, 2007.

* cited by examiner

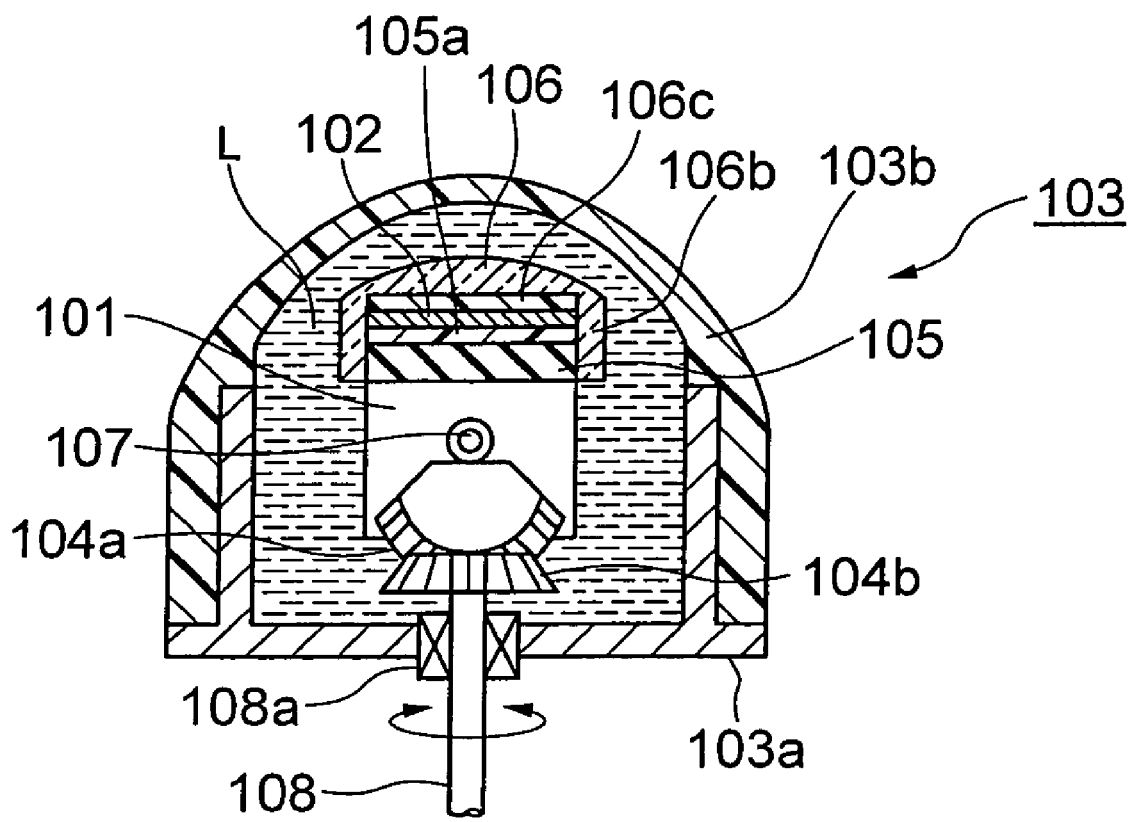

ULTRASONIC PROBE

TECHNICAL FIELD

The present invention relates to an ultrasonic probe in which a liquid serving as an ultrasonic wave medium is filled within a sealed container so as to perform mechanical scanning, in particular, to a short axis oscillating type ultrasonic probe (hereinafter, referred to as "short axis oscillating probe") that rotates and oscillates a piezoelectric element group in the short axis direction to obtain a three dimensional image of an examination subject.

BACKGROUND ART

1. Background of the Invention

A short axis oscillating probe is known as a probe that electronically scans a piezoelectric element group in the short axis direction thereof, and mechanically scans (oscillates) in the short axis direction thereof to obtain a three dimensional image of an examination subject (refer to Japanese Examined Patent Publication No. Hei 7-38851, Japanese Unexamined Patent Publication No. 2003-175033, Japanese Patent Application No. 2005-175700, and Japanese Unexamined Patent Publication No. 2005-334107 (FIG. 3, FIG. 5)). Consequently, such a probe has been brought to practical application because for example wiring (electrical connection) and scanning circuits thereof, can be made simpler, compared for example to a matrix type probe in which piezoelectric elements are arranged in lengthwise and crosswise array to be electronically scanned in a two-dimensional direction.

2. Prior Art

FIG. 3 is a drawing for explaining a conventional example of a short axis oscillating probe, wherein FIG. 3A is a sectional view in the long axis direction of a piezoelectric element group, and FIG. 3B is a sectional view in the short axis direction. The short axis oscillating probe is such that a piezoelectric element group 102 provided on a rotational retention base 101 is housed within a sealed container 103. The rotational retention base 101 is of a sectionally channel shape with leg sections 101a and 101b on both end sides of a horizontal section thereof, and on the horizontal section of the rotational retention base 101, there is arranged the piezoelectric element group 102. Moreover, on the inner side face of one of the leg sections 101b there is fixed a first bevel gear 104a.

The piezoelectric element group 102 is configured such that a large number of piezoelectric elements 102a are arranged in the long axis direction. Here it is fastened onto a backing member 105a on a curve-surfaced base 105 provided on the horizontal section of the rotational retention base 101. As a result, the ultrasonic probe is made as a so called convex type. On the surface of the piezoelectric element group 102, generally there is provided an acoustic matching layer 106c that brings acoustic impedance close to that of a living body (human body) to increase propagation efficiency, and on the top face of the acoustic matching layer 106c there is further provided an acoustic lens 106.

The sealed container 103 is joined by fitting together a container main body 103a and a cover 103b, the cross-sections of which are both concave shaped. On a pair of opposing side walls of the container main body 103a, there is provided a pair of rotational center shafts 7 that rotate and oscillate the rotational retention base 101 (the piezoelectric element group 102) in the short axis direction, and the rotational shafts 107 slidably engage with bearings 107a of the leg sections 101a and 101b on both end sides of the rotational retention base 101. A rotational shaft 108 connected to a rotating mechanism such as motor passes in a sealed condition through a bottom wall of the container main body 103a, and on the tip end of the rotational shaft 108 there is provided a second bevel gear 104b so as to mesh with the first bevel gear 104a.

The inside of the sealed container 103 is filled with a liquid that serves as an ultrasonic wave medium such as oil L that results in bringing the acoustic impedance close to that of a human body and with a low ultrasonic wave propagation loss. Accordingly, ultrasonic wave propagation loss between the inner circumferential surface of the cover 103b and the piezoelectric element group 102 (acoustic lens 106) becomes lower, and the acoustic impedance matching with a human body can be increased. Consequently ultrasonic wave propagation efficiency is increased. If air is present between the inner circumferential surface of the cover 103b and the surface of the piezoelectric element group 102, attenuation of the ultrasonic waves becomes significant and propagation efficiency becomes degraded. As a result, it is not possible to perform excellent transmission/reception of ultrasonic waves.

The oil L is filled from an inlet hole 110 provided in the bottom face of the container main body 103a. When injecting the oil L, the bottom face of the container main body 103 is faced upwards and the pre-degassed oil L is injected. Then, for example, a sealing ring (O ring) (not shown) is attached to the inlet hole 110, and the container main body 103 is sealed with a sealing lid 111a having a male thread.

A rotating mechanism 110 such as motor is covered by a back side surface cover 119, and a cable 118 to be connected to a diagnostic tool is led out from the back side surface cover 119. As a result, rotation of the second bevel gear 104b rotates and oscillates the first bevel gear 104a in the short axis direction, and the rotational retention base 101 (piezoelectric element group 102) integrated with this rotates and oscillates left and right about the center line that equally divides the short axis direction.

Problems in the Prior Art

However, in the conventional short axis oscillating probe configured as described above, for example as pointed out in Japanese Unexamined Patent Publication No. 2005-334107, there has been a problem in that the oil L filled within the sealed container 103 expands and contracts due to temperature change, causing oil leakage from the sealed container 103 and air bubbles. As a result, attenuation of the ultrasonic waves becomes significant, resulting in a significant reduction in the ultrasonic wave characteristics of the probe.

In order to avoid this problem, for example, there is disclosed in Japanese Unexamined Patent Publication No. 2005-334107 that for the inlet hole 110 of the oil L, there is separately provided a diaphragm 112 that links to the sealed container 103 and functions as an expansion and contraction section, and there is further provided an additional bubble accumulator. An opening and closing section is provided in the bubble accumulator mentioned in this publicly known document, however, a concrete description of this opening and closing section is absent. Therefore, the present invention basically takes the case of providing the diaphragm 112 as the prior art.

However, in such a conventional example, an exhaust hole is absent for the inlet hole 110, and there is only provided the diaphragm 112. Therefore, there is the problem described below. That is to say, the inlet hole 110 also serves as an exhaust hole, so that the inlet hole 110 and an exhaust hole are the same thing. In addition, the diameter thereof is small. As a result, there is a problem in that when filling the pre-degassed oil L, air inside the sealed container 103 is mixed in the oil L and cannot be completely discharged, causing the air to remain in the oil L as air bubbles.

For example, after filling the sealed container 103 with the oil L, air bubbles may be removed by an evacuated degassing device, and an additional amount of the oil L may be added. However, air bubbles still occur even in this case. Furthermore, in general the tip end of the diaphragm 112 is positioned higher than the inlet hole 110. Therefore it becomes difficult to remove air bubbles that have occurred inside the diaphragm 112 when injecting the oil L.

As a result, there has been a problem in that it is difficult to remove air bubbles that occur when filling the oil L, and to fully fill up only with oil, only by providing the diaphragm 112 in the sealed container 103 in addition to the inlet hole 110. These problems are observed not only in a short axis oscillating probe intended to comprise a piezoelectric element group (array type), but also for example in an ultrasonic probe with the piezoelectric elements in a circular shape as a single plate so as to perform mechanical scanning. In short, a problem occurs when filling a liquid that serves as an ultrasonic wave medium within the sealed container.

Object of the Invention

An object of the present invention is to provide an ultrasonic probe that prevents an occurrence of air bubbles in a liquid that serves as an ultrasonic wave medium, and that realizes excellent ultrasonic characteristics.

BRIEF DESCRIPTION OF THE DRAWINGS

FIG. 1 is a drawing for explaining an embodiment of a short axis oscillating probe of the present invention, wherein

FIG. 3 is a drawing for explaining a short axis oscillating probe of a conventional example, wherein FIG. 3B is a sectional view in the short axis direction.

DISCLOSURE OF THE INVENTION

The present invention configures an ultrasonic probe such that: a piezoelectric element is housed within a sealed container so as to be rotated and oscillated left and right about a center line that equally divides a plate surface of the piezoelectric element in the short axis direction; and the sealed container is filled with a liquid (oil) that serves as an acoustic medium, and in the sealed container there are provided a liquid inlet hole as well as an exhaust hole, to the inlet hole there is connected a flexible tube that functions as a diaphragm, and on the flexible tube and the exhaust hole there are respectively provided a sealing lid.

According to such a configuration, since there is provided the exhaust hole in addition to the inlet hole, for example, air within the sealed container can be easily discharged from the exhaust hole when injecting the liquid. Consequently, an occurrence (mix) of air bubbles when injecting the liquid can be reduced compared to the conventional example. Furthermore, easy removal of air bubbles after filling the liquid can be enabled with use of a degassing device (drawing a vacuum).

Moreover, with use of the flexible tube connected to the inlet hole or the exhaust hole as a pipette, air bubbles in the fully filled liquid can be suctioned and discharged. Consequently it becomes easier to fully fill up the sealed container with a liquid while suppressing air bubble occurrence therein.

Furthermore, since the flexible tube functions as a diaphragm, the volume capacity thereof freely changes according to an expansion and contraction of the liquid. As a result, after the liquid is fully filled and the sealing lid has been mounted on the exhaust hole, an occurrence of air bubbles can be suppressed even if there is an expansion and contraction in the liquid. Consequently, excellent ultrasonic characteristics are achieved.

Furthermore, in the present invention, to the exhaust hole there are connected two flexible tubes that function as diaphragms, and on the tip ends of which there are provided sealing lids. As a result, in particular after fully filling the liquid, these two flexible tubes function as diaphragms, and therefore for example the expansion and contraction amount of the oil may be flexibly allowed, compared to the case of having one flexible tube.

Furthermore, in the present invention, a plurality of the piezoelectric elements is arranged in a long axis direction so as to form a piezoelectric element group, and the center line equally divides a short axis direction of the piezoelectric element group. As a result, as a short axis oscillating probe, the probe can obtain three dimensional data and the ultrasonic characteristics thereof are even better.

BEST MODE FOR CARRYING OUT THE INVENTION

Figure 1A:
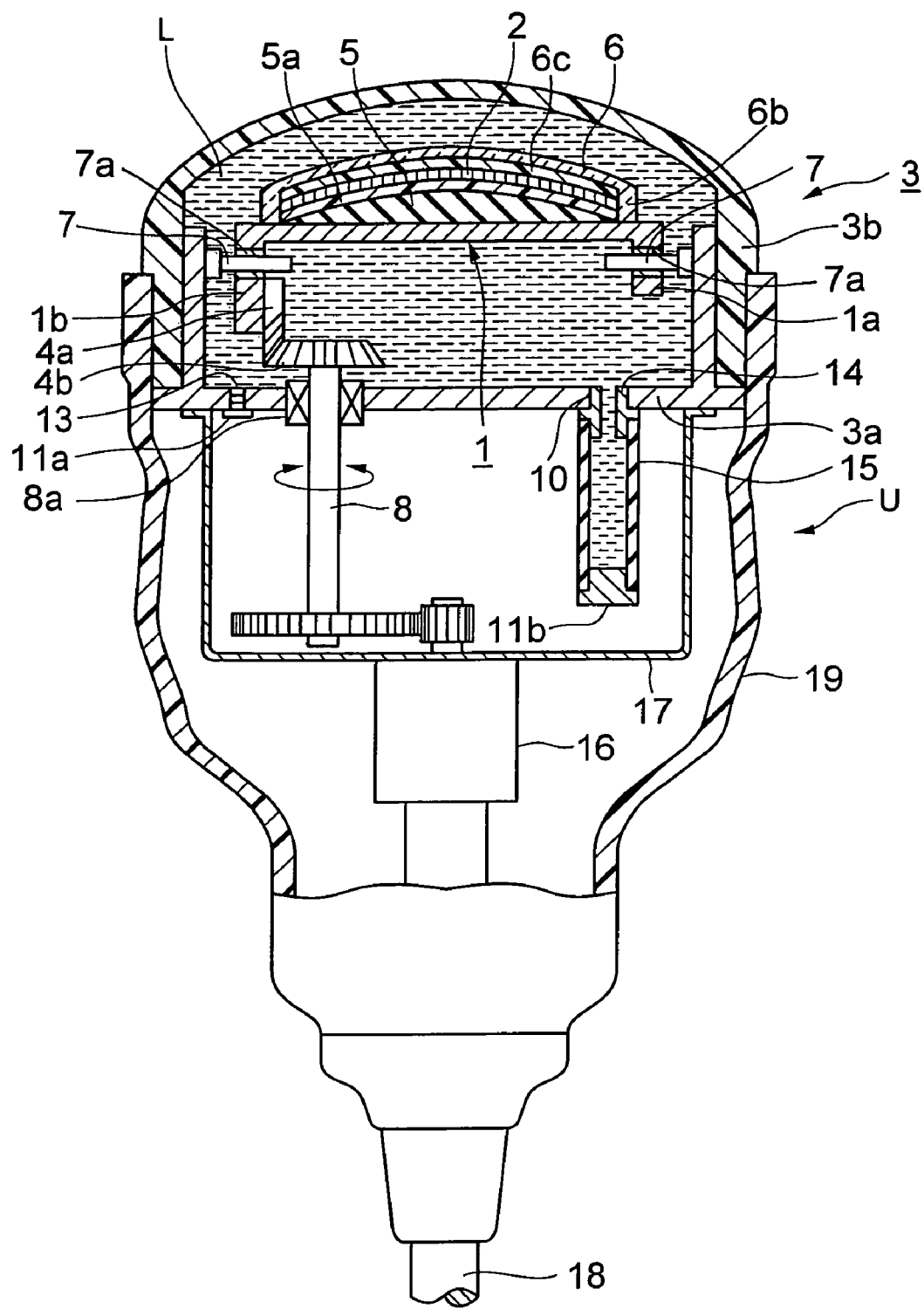
FIG. 1A is a sectional view in the long axis direction.
Figure 1B:
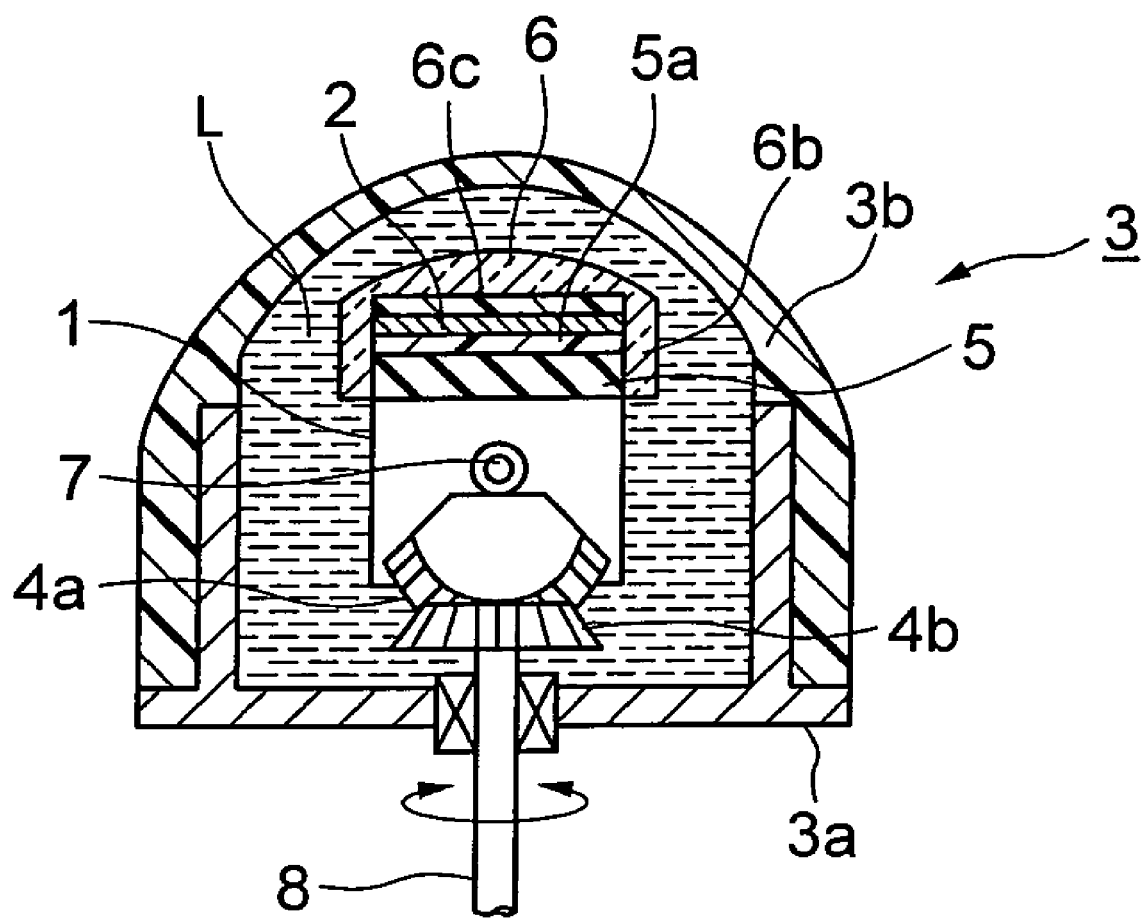
FIG. 1B is a sectional view in the short axis direction.

FIG. 1A is a sectional view in the long axis direction for explaining an embodiment of a short axis oscillating probe of the present invention.

The short axis oscillating probe of the present invention is such that a piezoelectric element group 2 arranged in the long axis direction is provided on a horizontal section of a sectionally channel shaped rotational retention base 1, so as to be housed within a sealed container 3 comprising a container main body 3a and a cover 3b that are both sectionally concave shaped. In leg sections 1a and 1b on both end sides of the rotational retention base 1, there is respectively provided a bearing 7a so as to slidably engage with a pair of rotational center shafts 7 provided, in the long axis direction, on the side walls of the container main body 3a.

A first bevel gear 4a that is provided on one leg section 1b of the rotational retention base 1 and that rotates and oscillates in the short axis direction, meshes with a second bevel gear 4b fastened onto a rotational shaft 8 that passes in a sealed condition through the bottom wall of the sealed container 3. Thereby, the rotational retention base 1 (piezoelectric element group 2) rotates and oscillates left and right about the center line that equally divides the short axis direction of the piezoelectric element group 2. Here, within the sealed container 3 there is filled a liquid such as oil L that serves as an ultrasonic wave medium.

Furthermore in this embodiment of the present invention, in the bottom face of the container main body 3a there is arranged an inlet hole 10 along with an exhaust hole 13. In the inlet hole 10 there is provided a cross shaped guiding screw 14 having a through hole, and one end side, on which the screw is provided (upper part in the drawing), is screwed into a thread formed on the inner circumference of the inlet hole 10. Between the inlet hole 10 and the guiding screw 14, there is interposed an adhesive agent for example, so as to provide further reliable sealing therebetween.

To the other end side of the guiding screw 14 (lower part in the drawing), there is connected a flexible tube 15, both ends of which are open, formed from fluororubber, which is highly resistant to chemicals and oils. For example, one end side of the flexible tube 15 is press-fitted thereon, with an adhesive agent interposed on the other end side of the guiding screw 14. Alternatively, it is sealed by placing a separate band over the flexible tube 15.

Moreover the other end side of the flexible tube 15 is closed off (sealed) by a convex shaped sealing lid 11b that uses an adhesive agent, for example. Around the exhaust hole 13 there is provided a sealing ring (O ring) for example, and the exhaust hole 13 is sealed with a sealing lid 11a having a male thread.

Furthermore, in a state where one end side of the flexible tube 15 has been attached to the guiding screw 14 and then the sealing lid 11a on the exhaust hole 13 is opened, first, oil L that serves as an ultrasonic wave medium is injected from the other end side of the flexible tube 15 into the flexible tube 15 up to approximately 70 percent of the tube capacity. In this case, the oil L that has been pre-degassed is injected. Next, after injecting the oil L, air bubbles that occurred during injection are removed for example by the evacuated degassing device.

Subsequently, an additional amount of the oil L that has been degassed is poured in from the other end of the flexible tube 15 so as to overflow from the exhaust hole 13. In this state, the sealing ring is placed and the sealing lid 11a is screwed on. Then, the flexible tube 15 is pressed and released so as to suck in and discharge any remaining air bubbles, and an additional amount of the oil L is further added. Then this sequence is repeated until the oil L is filled to full. Lastly, this is left to stand to cool down, and then an amount that has been reduced due to the cooling is added to fill the oil L to full, and the other end side of the flexible tube 15 is sealed with the sealing lid 11b.

According to such a configuration, air flows out from the exhaust hole 13 when the oil L is injected from the other end side of the flexible tube 15. Therefore, air bubbles are less unlikely to occur in the injected oil L compared to the conventional case where there is no exhaust hole 13 provided. Consequently removal of air bubbles with use of a degassing device becomes relatively easy, depending on the amount of the oil L.

Moreover, since the flexible tube 15 that functions as a diaphragm is connected to the inlet hole 10, air bubbles can be easily taken out from the inlet hole 10 using the flexible tube 15 as a pipette when the sealed container 3 is fully filled with the oil L. Consequently it is easy to fill the sealed container 3 only with the oil L containing no bubbles.

Furthermore, since the flexible tube 15 functions as a diaphragm, the volume capacity thereof changes freely according to the expansion and contraction of the liquid. As a result, once the oil L has been filled in and the sealing lids 11b and 11a have been mounted on the inlet hole 10 and the exhaust hole 13, even if there is an expansion and contraction of the oil L filled within the sealed container 3, any occurrence of air bubbles is suppressed. As a result, in the present embodiment, the ultrasonic wave characteristics of the short axis oscillating probe can be made even better.

Figure 2:
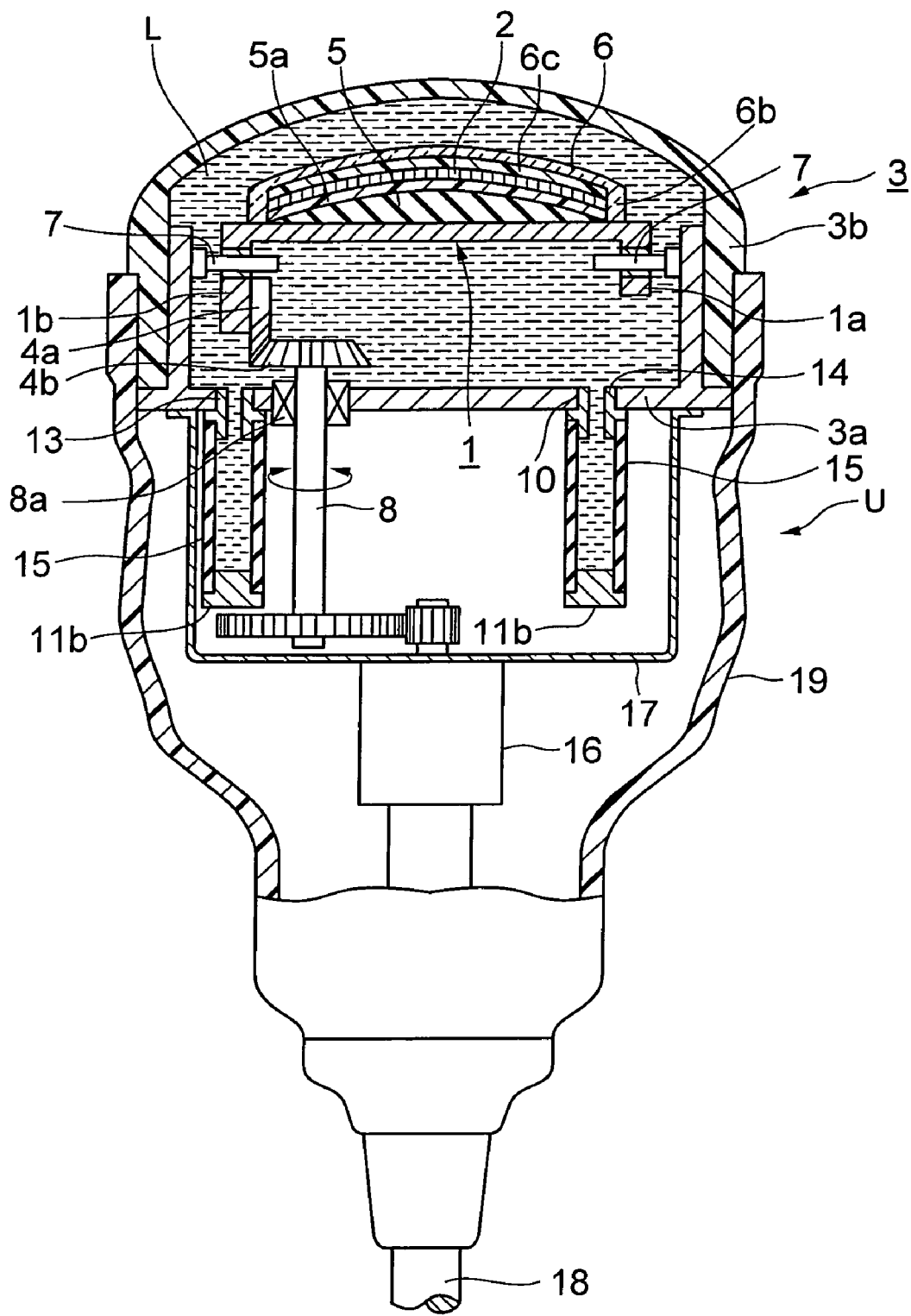
FIG. 2 is a sectional view in the long axis direction for explaining another embodiment of the short axis oscillating probe of the present invention.
Figure 3A:
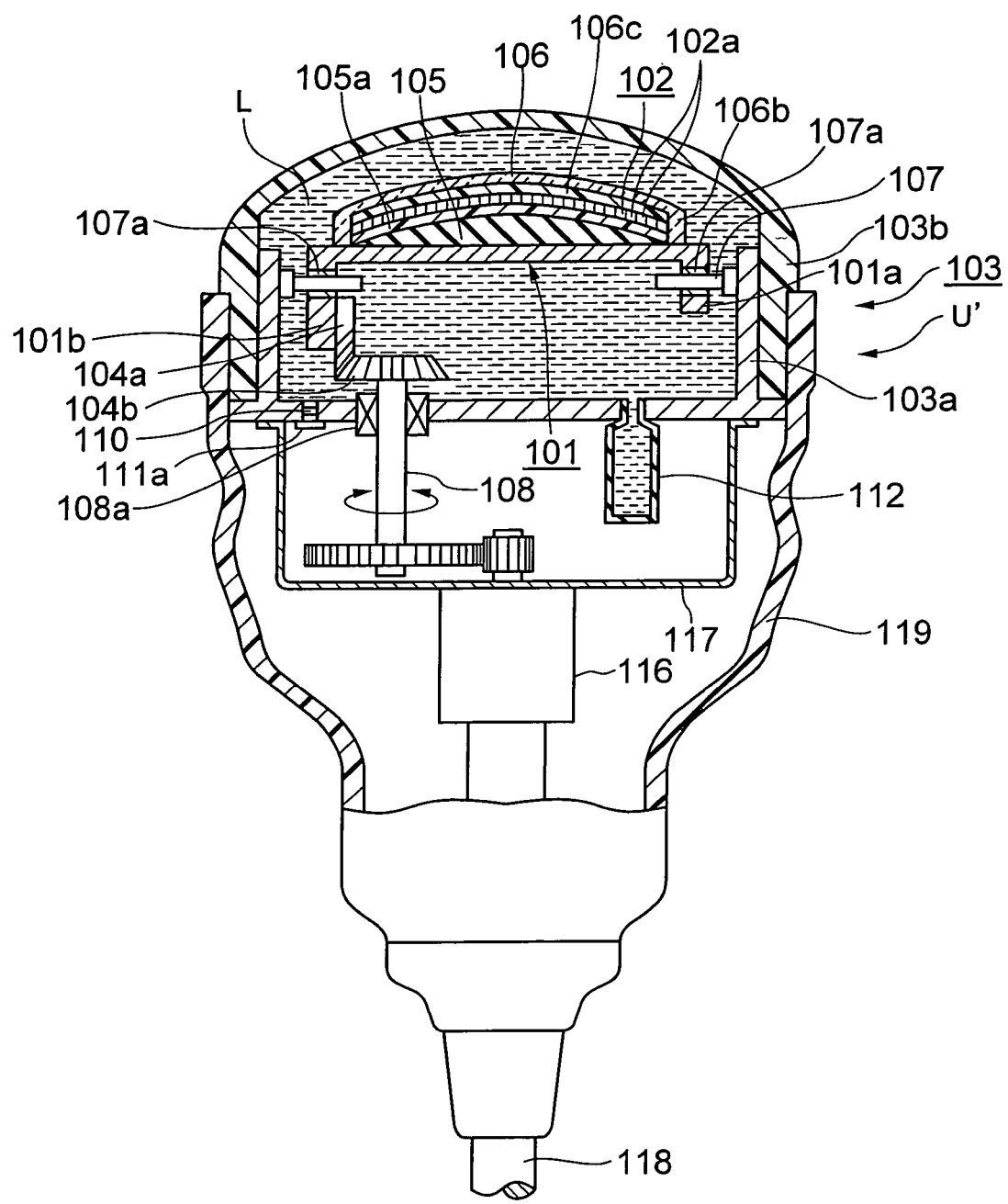
FIG. 3A is a sectional view in the long axis direction.

The flexible tube 15 is provided only on the inlet hole 10 in the above embodiment. However, as shown in FIG. 2, it may be further provided on another exhaust hole 13. In this case, for example the flexible tube 15 of the exhaust hole 13 should be made shorter than that of the other flexible tube 15 so that the oil L can be easily overfilled when filling it up from the inlet hole 10. As a result, particularly once the sealed container 3 has been fully filled with the oil L and the sealing lids 11a and 11b have been attached, two of these flexible tubes 15 function as diaphragms. Therefore, for example expansion and contraction of the oil L may be flexibly allowed within the sealed container 3.

Moreover, the present invention has been described as a short axis oscillating probe, however, it may be similarly applied to a case of generic mechanical scanning where the piezoelectric element group 2 is a single plate, for example in a circular shape, and rotates and oscillates left and right about the center line that equally divides the plate surface.

INDUSTRIAL APPLICABILITY

The short axis oscillating probe of the present invention can be widely used for forming a three dimensional image of an examination subject such as a human body.

The invention claimed is:

1. An ultrasonic probe comprising a piezoelectric element housed within a sealed container so as to be rotated and oscillated left and right about a center line of the sealed container that equally divides a plate surface of said piezoelectric element wherein said sealed container is filled with a liquid that serves as an acoustic medium with said sealed container being provided with a liquid inlet hole and a separate exhaust hole each formed on a bottom wall of the sealed container wherein both said inlet hole and said exhaust hole formed on the bottom wall of the sealed container are connected to a respective flexible tube that functions as a diaphragm and on each-said flexible tube there is respectively mounted a sealing lid.

2. An ultrasonic probe according to claim 1, wherein a plurality of said piezoelectric elements are arranged in a long axis direction so as to form a piezoelectric element group, and said center line equally divides a short axis direction of said piezoelectric element group.

3. An ultrasonic probe according to claim 1, wherein a plurality of said piezoelectric elements are arranged in a long axis direction so as to form a piezoelectric element group on the piezoelectric element and said center line equally divides a short axis direction of said piezoelectric element group.

4. An ultrasonic probe comprising:
a sealed container operative and configured to be rotated and oscillated left and right about a center line wherein the sealed container is provided with:
a liquid inlet hole formed on a bottom wall of the sealed container;
an exhaust hole formed on the bottom wall of the sealed container;
a first flexible tube coupled to the liquid inlet hole in an interior portion of the sealed container wherein the first flexible tube is operative to function as a liquid diaphragm; and
a piezoelectric element housed in the sealed container.

5. An ultrasonic probe as recited in claim 4 further including a second flexible tube coupled to the exhaust hole in an interior portion of the sealed container wherein the second flexible tube is operative to function as a liquid diaphragm.

6. An ultrasonic probe as recited in claim 4 further including a sealing lid respectively provided on each of the liquid inlet hole and the exhaust hole.

* * * * *